United States Patent
Flohr et al.

(10) Patent No.: US 9,044,189 B2
(45) Date of Patent: Jun. 2, 2015

(54) METHOD AND COMPUTED TOMOGRAPHY SYSTEM FOR GENERATING WEIGHTED TOMOGRAPHIC IMAGE DATASETS

(75) Inventors: Thomas Flohr, Uehfeld (DE); Gabriel Haras, Mücke (DE); Daniel Niederlöhner, Erlangen (DE); Stefan Pflaum, Hirschaid (DE)

(73) Assignee: Siemens Aktiengesellschaft, Munich (DE)

( * ) Notice: Subject to any disclaimer, the term of this patent is extended or adjusted under 35 U.S.C. 154(b) by 366 days.

(21) Appl. No.: 13/478,572

(22) Filed: May 23, 2012

(65) Prior Publication Data

US 2012/0301002 A1    Nov. 29, 2012

(30) Foreign Application Priority Data

May 24, 2011    (DE) .......................... 10 2011 076 346

(51) Int. Cl.
| | |
|---|---|
| G06K 9/00 | (2006.01) |
| A61B 6/00 | (2006.01) |
| A61B 6/03 | (2006.01) |
| G01T 1/29 | (2006.01) |

(52) U.S. Cl.
CPC .............. *A61B 6/4241* (2013.01); *A61B 6/032* (2013.01); *A61B 6/4233* (2013.01); *A61B 6/482* (2013.01); *A61B 6/5235* (2013.01); *G01T 1/2985* (2013.01)

(58) Field of Classification Search
None
See application file for complete search history.

(56) References Cited

U.S. PATENT DOCUMENTS

| | | | | |
|---|---|---|---|---|
| 7,272,429 | B2* | 9/2007 | Walker et al. | 600/407 |
| 7,372,934 | B2 | 5/2008 | De Man et al. | |
| 7,433,443 | B1 | 10/2008 | Tkaczyk et al. | |
| 7,583,779 | B2* | 9/2009 | Tkaczyk et al. | 378/4 |
| 8,619,943 | B2* | 12/2013 | Flohr et al. | 378/5 |
| 2005/0061985 | A1 | 3/2005 | Hoffman | |

(Continued)

FOREIGN PATENT DOCUMENTS

| | | |
|---|---|---|
| CN | 1985765 A | 6/2007 |
| CN | 101011251 A | 8/2007 |

(Continued)

OTHER PUBLICATIONS

Chinese Office Action and English translation thereof dated Mar. 3, 2014.

(Continued)

*Primary Examiner* — Tahmina Ansari
(74) *Attorney, Agent, or Firm* — Harness, Dickey & Pierce, P.L.C.

(57) ABSTRACT

A method and a computed tomography system are disclosed for generating tomographic image datasets of a measurement object. The computed tomography system includes at least two simultaneously operable sets of detector elements which jointly scan a measurement object from a multiplicity of projection angles in an integrating manner on the one hand and an energy-resolving manner on the other hand. In at least one embodiment, the method includes determining a first projection dataset from measurement data recorded in an integrating manner. Further, at least one second projection dataset is determined from energy-resolved measurement data, and in addition a weighted tomographic result image dataset is calculated based on weighted use of the first and the second projection dataset, the weighting being applied to the projection data or the tomographic image data reconstructed therefrom.

26 Claims, 3 Drawing Sheets

(56) References Cited

U.S. PATENT DOCUMENTS

| | | |
|---|---|---|
| 2005/0173641 A1 | 8/2005 | Yanoff |
| 2007/0147574 A1* | 6/2007 | Bernard De Man et al. ..... 378/4 |
| 2007/0153979 A1 | 7/2007 | Baumann et al. |
| 2007/0183562 A1 | 8/2007 | Popescu et al. |
| 2007/0189449 A1 | 8/2007 | Baumann et al. |
| 2007/0205367 A1* | 9/2007 | Deman et al. ............ 250/363.02 |
| 2008/0101534 A1 | 5/2008 | Shaughnessy |
| 2008/0260092 A1 | 10/2008 | Imai et al. |
| 2009/0122953 A1 | 5/2009 | Imai |
| 2009/0147919 A1 | 6/2009 | Hirokawa et al. |
| 2009/0154640 A1 | 6/2009 | Baumann et al. |
| 2010/0220834 A1 | 9/2010 | Heismann et al. |
| 2012/0300896 A1* | 11/2012 | Flohr et al. ........................ 378/5 |
| 2012/0301001 A1* | 11/2012 | Flohr et al. ................... 382/131 |
| 2012/0301002 A1* | 11/2012 | Flohr et al. ................... 382/131 |
| 2013/0108013 A1* | 5/2013 | Leng et al. ..................... 378/19 |

FOREIGN PATENT DOCUMENTS

| | | |
|---|---|---|
| CN | 101011256 A | 8/2007 |
| CN | 101175440 A | 5/2008 |
| CN | 101249000 A | 8/2008 |
| CN | 101375798 A | 3/2009 |
| CN | 101433464 A | 5/2009 |
| JP | 2007-120557 | 5/2007 |
| JP | 2009261456 A | 11/2009 |
| WO | WO 2007087789 A1 | 8/2007 |

OTHER PUBLICATIONS

German Office Action for German Application No. 10 2011 076 346.5.

German Priority Document DE 10 2011 076 346.5 filed May 24, 2011 (not yet published).

* cited by examiner

METHOD AND COMPUTED TOMOGRAPHY SYSTEM FOR GENERATING WEIGHTED TOMOGRAPHIC IMAGE DATASETS

PRIORITY STATEMENT

The present application hereby claims priority under 35 U.S.C. §119 to German patent application number DE 10 2011 076 346.5 filed May 24, 2011, the entire contents of which are hereby incorporated herein by reference.

FIELD

At least one embodiment of the invention generally relates to a method and/or a computed tomography system for generating tomographic image datasets of a measurement object with the aid of a computed tomography system (CT system) having at least two simultaneously operable sets of detector elements which jointly scan a measurement object from a multiplicity of projection angles, wherein at least one first set of integrating detector elements measures incident radiation over the entire energy spectrum of the incident radiation in an integrating manner and at least one second set of counting detector elements measures incident radiation in at least two energy ranges in a resolving manner.

BACKGROUND

Dual-source CT systems having a conventional integrating scintillation detector and a counting detector are generally known. In such applications both measurement systems are operated simultaneously in order to scan a measurement object, in most cases a patient. Such a dual-source CT system in this case contains two emitter-detector systems, each including an X-ray emitter and the respectively associated detector, which are disposed offset at an angle to each other on a gantry.

SUMMARY

A problem with measurements using energy-selective counting detectors resides in the relatively high drift of such detectors as a result of a preceding irradiation.

At least one embodiment of the invention is directed to a method and/or a computed tomography system for scanning a measurement object and generating tomographic image datasets from such scans in which it is not necessary to calibrate the counting detector elements prior to each measurement in order to compensate for the drift of the detector elements.

According to at least one embodiment of the present inventive concepts, the inventors propose improving a method for generating tomographic image datasets of a measurement object with the aid of a computed tomography system (CT system) having at least two simultaneously operable sets of detector elements which jointly scan a measurement object from a multiplicity of projection angles, the method comprising at least the following wherein:

incident radiation is measured over the entire energy spectrum of the incident radiation in an integrating manner by means of at least one first set of integrating detector elements and defined as the first projection dataset, and incident radiation is measured in at least two energy ranges in a resolving manner by means of at least one second set of counting detector elements and defined as the second projection dataset.

In addition to the method according to at least one embodiment of the invention, a computed tomography system (CT system) is also proposed, comprising:

at least two simultaneously operable sets of detector elements for simultaneously scanning an examination object from a multiplicity of projection angles, wherein at least one first set of integrating detector elements is configured for integrating radiation measurement, and at least one second set of counting detector elements is configured for resolving an incident radiation spectrum into at least two energy bins, and a computer system for analyzing measurement results of the detector elements, said computer system having a memory and computer programs resident therein, wherein also present in the memory of the computer system is at least one computer program which during operation performs the above-described method.

Advantageous developments of the invention are the subject matter of subordinate claims.

BRIEF DESCRIPTION OF THE DRAWINGS

The invention is described in more detail below with the aid of the figures, wherein only the features necessary to an understanding of the invention are shown. The following reference signs are used: 1: CT system; 2: first X-ray tube; 3: first detector; 4: second X-ray tube; 5: second detector; 6: gantry housing; 7: patient; 8: patient couch; 9: system axis; 10: computer system; 11: contrast agent applicator; 12: ECG line; I: integrating detector element; Prg1-Prgn: computer programs; Z: counting detector element.

Specifically in the Figures.

Figure 1:
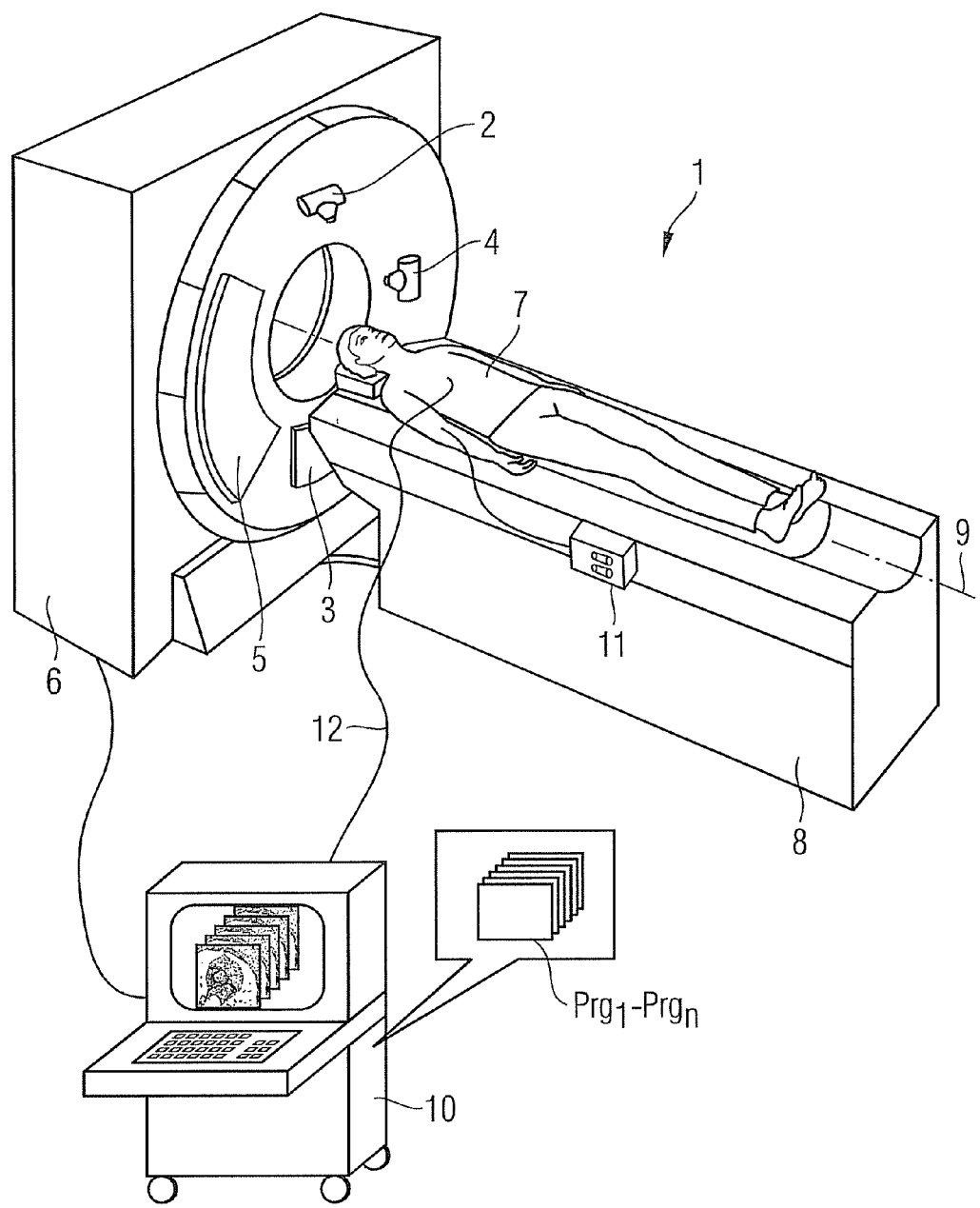
FIG. 1: shows a CT system.

It should be noted that these Figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. The use of similar or identical reference numbers in the various drawings is intended to indicate the presence of a similar or identical element or feature.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The inventors have recognized the following:

Computed tomography (CT) devices employed in the medical environment are nowadays equipped with integrating scintillation detectors as the state of the art. The incident X-rays are initially converted therein in a two-stage process into visible light, which is then detected by downstream photodiodes and transformed into electrical signals. Examples of corresponding scintillators are gadolinium oxide or gadolinium oxide sulfide. Such scintillation detectors have a very wide dynamic range and can process the minimum and maximum X-ray flux densities used in medical computed tomography without difficulty. On the other hand their spatial resolution is limited, since for mechanical reasons the detector pixels cannot be reduced in size at will for purposes of mechanical and optical separation due to inactive dead zones between the pixels. Furthermore, integrating scintillation detectors do not supply any spectral information, so that material characteristic differences in X-ray absorption at different energies of the X-ray spectrum cannot be measured directly. Also, the contrast-to-noise ratio of the detected signals from integrating detectors is not optimal because the low-energy quanta that carry the most contrast information are also assigned only a low weighting in the integrating detector in accordance with their low energy, so that the contrast of certain materials, such as white and gray brain matter for example, is reduced as a result.

In contrast thereto there exist counting detectors in which the incident X-ray quanta are converted into electrical signals and counted in a direct process. Examples of corresponding detector materials are cadmium telluride or cadmium zinc telluride. Counting detectors can be very finely structured on their surface since the pixels do not have to be mechanically separated and therefore dead zones are eliminated. A significantly higher spatial resolution is therefore possible than with conventional integrating scintillation detectors. In addition the incident X-ray quanta can be detected for a spectral resolution into different energy bands, as a result of which material characteristic differences in X-ray absorption at different energies can be registered with a single measurement. Thanks to the possibility of energy-dependent weighting of the contributions to the overall signal it is furthermore possible to improve the object contrast and hence the contrast-to-noise ratio in comparison with integrating scintillation detectors.

A disadvantage of counting detectors, however, is the limited dynamic range as a result of the detector materials employed, in which a maximum X-ray flux density must not be exceeded, which according to the current prior art is not high enough for unrestricted use in a medical CT system. A further disadvantage is the high drift of the signals from a counting detector after a preceding irradiation, with artifacts that are difficult to correct being produced in the images under certain conditions.

However, these disadvantages can be counterbalanced if, during the calculation of a tomographic image dataset from the measurement data acquired with integrating and counting detector elements, a weighted overlay takes place for the assessment of the weighting, in particular while simultaneously taking into account characteristics of the respective measurement as well as characteristics of the measurement object, in particular their local or measurement-point-related characteristics. Specifically, the following criteria in particular can be considered here:

Measurement data of the integrating scintillation detector and of the counting detector recorded at the same position of the measurement object is overlaid in a weighted manner, wherein e.g. the measurement values of the scintillation detector make the main contribution in regions of high photon flux and the measurement values of the counting detector make the main contribution in regions of low photon flux.

CT images of the integrating scintillation detector and of the counting detector recorded at the same position of the measurement object are overlaid in a weighted manner, wherein the highly resolved image of the counting detector makes the main contribution in regions having a high object contrast and fine structures (e.g. bones, inner ear, . . . ), while the poorer resolution, but lower noise image of the scintillation detector makes the main contribution in other regions.

CT images of the integrating scintillation detector and of the counting detector recorded at the same position of the measurement object are overlaid in a weighted manner, wherein in certain object regions spectral information of the counting detector, e.g. material characteristic differences in X-ray absorption at different energies refined by means of postprocessing, is selectively merged with the CT image of the integrating scintillation detector.

CT images of the integrating scintillation detector and of the counting detector recorded at the same position of the measurement object are overlaid in a weighted manner by means of a weighting function which can be easily varied by the user when studying the images, in order to be able to toggle back and forth between a conventional CT image of the integrating scintillation detector and a CT image of the counting detector exhibiting increased contrasts.

The above-cited embodiment variants relate in each case to separate detectors having different types of detector elements, i.e. with in each case exclusively integrating or exclusively counting detector elements. Also included within the scope of the invention, however, are hybrid detectors which have both integrating and counting detector elements.

According to at least one embodiment of the present inventive concepts, the inventors propose improving a method for generating tomographic image datasets of a measurement object with the aid of a computed tomography system (CT system) having at least two simultaneously operable sets of detector elements which jointly scan a measurement object from a multiplicity of projection angles, the method comprising at least the following wherein:

incident radiation is measured over the entire energy spectrum of the incident radiation in an integrating manner by means of at least one first set of integrating detector elements and defined as the first projection dataset, and incident radiation is measured in at least two energy ranges in a resolving manner by means of at least one second set of counting detector elements and defined as the second projection dataset.

An improvement of at least one embodiment resides in a tomographic result image dataset being calculated from the first and second projection dataset, wherein data originating from the first and second projection dataset—in other words, both projection data and reconstructed image data—is assigned a weighting.

Prior to the weighting, a first CT image dataset and a second CT image dataset can in this case advantageously be reconstructed using the first projection dataset and the second projection dataset, respectively.

On the basis of previously separately reconstructed CT image datasets, the first CT image dataset can now be overlaid with the second CT image dataset in a weighted manner using an inter-dataset weighting factor in each case in order to produce the CT result image dataset.

Alternatively, in order to take account also of local characteristics of the image datasets or of the measurement object, the first CT image dataset can also be overlaid with the second CT image dataset in a weighted manner using locally different weighting factors in order to produce the CT result image dataset.

This consideration of local characteristics of the measurement object or of the tomographic image of the measurement object can be realized in that the first and/or second CT image dataset are/is subdivided into a multiplicity of subregions in which object-specific characteristics are measured which are systematically mapped with different degrees of quality in the first or second CT image dataset, and the local weighting factor is chosen as a function of the object-specific characteristic.

The maximum contrast in the respective subregions or the fineness of the structures in the subregions can particularly advantageously be defined as an object-specific characteristic and used for adjusting the respective local weighting factor.

Furthermore, a weighting function having at least one coefficient can also be used for weighting the previously reconstructed image data, and the at least one coefficient can be varied manually while studying the CT image being newly generated in each case.

If, however, the projection data is considered instead of the reconstructed image data, it is possible initially, depending on the type of detector elements—i.e. integrating or counting— to form a first and a second projection dataset, to overlay the first and second projection dataset in a weighted manner to produce a new projection dataset, and to reconstruct a CT result image dataset from the new projection dataset.

In this instance, too, an individual weight extending across projection datasets can be chosen according to the invention for the first and for the second projection dataset in each case.

However, a much more favorable variant of at least one embodiment of the method resides in carrying out a locally individual weighting of the projection datasets.

Such a locally individual weighting of the projection datasets can then—at least also—be carried out as a function of the locally measured photon flux, wherein the measurement data of the integrating detector elements at least tends to be more strongly rated at sites of higher photon flux than the measurement data of the counting detector elements, and the measurement data of the counting detector elements at least tends to be more strongly rated at sites of lower photon flux than the measurement data of the integrating detector elements. By means of said measure the characteristics of the integrating detector elements with their significantly higher dynamic range and more favorable noise values and the characteristics of the counting detector elements can be used with a potentially better spatial resolution, a present energy resolution and a superior value accuracy and/or linearity in the low-dosage range.

Accordingly, also in addition or alternatively to the weighting based on the size of the local photon flux, the locally individual weighting of the projection datasets can be carried out at least also as a function of a locally determined spatial frequency or average size of the spatial frequency or average frequency of the local spatial frequencies, wherein the measurement data of the integrating detector elements at least tends to be more strongly rated at sites of lower values than the measurement data of the counting detector elements, and vice versa.

Owing to the available energy resolution by way of the counting detector elements, in addition to a CT result image dataset, a material separation can also be carried out at least in relation to structurally or where applicable manually predefined subregions of the measurement object at least with the aid of the energy-resolved measurement values of the counting detector elements and the result thereof can be overlaid on the CT result image dataset.

In addition to the method according to at least one embodiment of the invention, a computed tomography system (CT system) is also proposed, comprising:

at least two simultaneously operable sets of detector elements for simultaneously scanning an examination object from a multiplicity of projection angles, wherein at least one first set of integrating detector elements is configured for integrating radiation measurement, and at least one second set of counting detector elements is configured for resolving an incident radiation spectrum into at least two energy bins, and a computer system for analyzing measurement results of the detector elements, said computer system having a memory and computer programs resident therein, wherein also present in the memory of the computer system is at least one computer program which during operation performs the above-described method.

In a first advantageous embodiment of the computed tomography system the at least one first set of integrating detector elements and the at least one second set of counting detector elements can in each case be arranged on physically different detectors.

Alternatively, however, the at least one first set of integrating detector elements and the at least one second set of counting detector elements can also be arranged on one detector, preferably the only detector present. As a result hereof the substantially more expensive counting detector elements would be at least partially compensated for by the saving resulting from the no longer required second emitter-detector system.

In this case the integrating detector elements of the at least one first set and the counting detector elements of the at least one second set can advantageously be arranged grouped in lines or alternatively in rows to form the one detector.

In another embodiment the integrating detector elements of the at least one first set and the counting detector elements of the at least one second set can also be arranged grouped in a checkerboard pattern to form said one detector.

The integrating detector elements of the at least one first set can furthermore be arranged in a plurality of directly adjacent lines and the counting detector elements of the at least one second set in a plurality of lines adjoining same on at least one detector. Basically, this is equivalent to two parallel, adjoining multiline detectors comprising different detector elements, both of which can be operated with a single emitter. As a result hereof, depending on the forward feed rate used in a spiral scan, either the entire detector can be used with the minimum possible scanning redundancy. Alternatively—if a redundant scan by way of counting and integrating parts of the detector is desired—a forward feed rate can be selected which ensures that the two different sets of detector lines can each scan the measurement object completely, such that all the projections, both with data of the counting and with data of the integrating detector elements, are present.

The populated surface of each of the counting detector elements can furthermore be embodied to be smaller in area than the surface of each of the integrating detector elements. A significantly higher spatial resolution can thus be achieved at least for the counting detector elements.

FIG. 1 shows an example of a CT system 1 having two emitter-detector systems on a gantry (not shown in further detail) in a gantry housing 6. The two emitter-detector systems, including a first X-ray tube 2 with an oppositely disposed detector 3 associated with the first X-ray tube on one side and of a second X-ray tube 4 with an oppositely disposed detector 5 associated with the second X-ray tube on the other side, are arranged on the gantry offset at an angle in a plane of rotation. According to the invention, the two detectors 3 and 5 can in each case be equipped with detector elements having different functions, such that one detector is fitted with counting detector elements and the other detector with integrating detector elements. Alternatively it is also possible for the detectors or at least one detector to be hybridized, whereby partly integrating, partly counting detector elements are installed in one detector. With regard to exemplary layouts of the differently operating detector elements, reference is also made to FIGS. 2 to 5.

Both emitter-detector systems sweep over a field of view located in the central circular bore. The patient 7 can be moved through said field of view along the system axis 9 with the aid of the patient couch 8. In principle, both a spiral scan and a sequential scan can be performed using said arrangement. In order to improve the imaging of blood vessels or other structures, the patient can also be injected with a contrast agent administered by way of the contrast agent applicator 11. Furthermore, cardiac actions can also be scanned via the ECG line 12 in order to perform a cardiac-action-triggered scan and/or reconstruction.

The CT system 1 is controlled and the scan of the patient 7 analyzed by the computer system 10 connected thereto, the computer system 10 having at least one memory in which computer programs Prg1-Prgn are stored. Also contained in the memory according to embodiments of the invention are programs which are embodied in such a way that during operation of the system they perform the different embodiments of the inventive method.

Examples of different mixed arrangements of integrating and counting detector elements in a detector of a CT system, which in some cases may also be the only detector, are shown in FIGS. 2 to 5.

Figure 2:
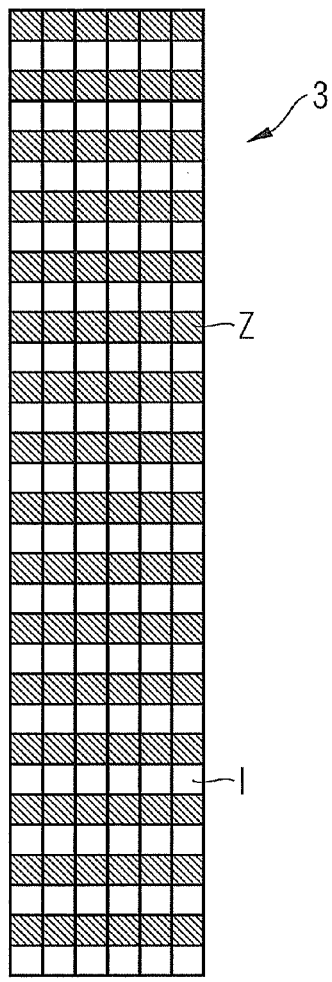
FIG. 2: shows a view from above onto a detector having integrating detector elements grouped in rows on one side and counting detector elements on the other.

FIG. 2 shows an embodiment of a hybrid detector having integrating (drawn without hatching) and counting (identified by hatching) detector elements I, Z arranged in alternate rows. Such an arrangement is suitable in particular in the case of orbital scans, since in this case each integrating detector element I is followed in the course of a revolution by a counting detector element Z and it is very easy to find congruent beams through the scanned measurement object having been scanned by both types of detector elements I, Z in order to compare these and if necessary to be able to make a correction to the measurement data of the counting detector elements Z.

Figure 3:
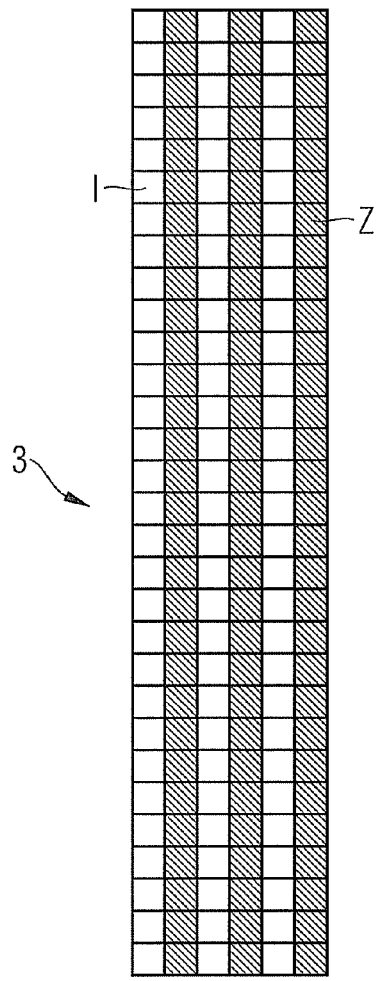
FIG. 3: shows a view from above onto a detector having integrating detector elements grouped in lines on one side and counting detector elements on the other.

The layout shown in FIG. 3 appears advantageous in particular for use in spiral scans. In this case integrating (drawn without hatching) and counting (identified by hatching) detector elements I, Z are arranged in alternate lines. Since a forward feed in the system axis direction is executed in the case of a spiral scan, identical or at least approximately identical beams through the measurement object again sweep over both types of detector elements I, Z in order to allow comparison of the associated measurement results and if necessary to enable a correction to be made to the measurement data of the counting detector elements Z. If it is not possible to find precisely overlapping beams from both sets of measurement data, there exists the possibility to identify interpolated measurement data for congruent beams, where applicable also beams in the opposite direction, by means of appropriate interpolation operations that are known per se.

It is pointed out that it also lies within the scope of at least one embodiment of the invention to use smaller (in terms of their projection surface area) detector elements Z for the counting detectors than is possible in the case of the integrating detector elements I. For example, each surface of a counting detector element Z shown here can also be subdivided several times, e.g. into 2×2, 3×3 or 4×4 separately readable subsidiary surfaces, as a result of which a much higher spatial resolution is produced.

Figure 4:
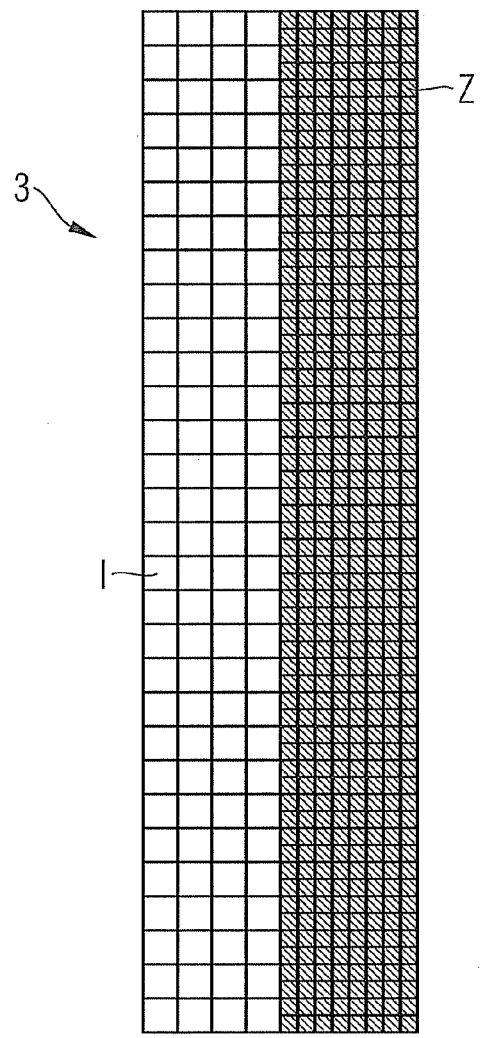
FIG. 4: shows a view from above onto a detector having a plurality of directly adjacent lines including integrating detector elements on one side and, adjoining these, a plurality of directly adjacent lines including counting detector elements on the other side.

FIG. 4 shows a view from above onto a detector having a plurality of directly adjacent lines including integrating detector elements I on one side and, adjoining these, a plurality of directly adjacent lines including counting detector elements Z on the other side. The integrating detector elements I are again depicted without hatching and the counting detector elements Z as hatched. Furthermore, the counting detector elements Z are embodied as only half the size in terms of their dimensions or, to put it another way, the spatial measurement resolution of the counting detector elements Z is twice as high as that of the integrating detector elements I.

Figure 5:
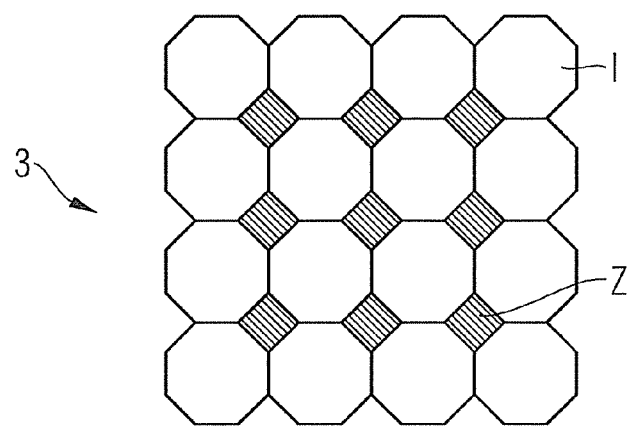
FIG. 5: shows a view from above onto a detector having octagonal integrating detector elements arranged in a honeycomb pattern and counting detector elements in the gaps.

Another advantageous variant of a hybrid arrangement of counting and integrating detector elements Z, I is shown in FIG. 5. In this case the integrating (shown without hatching) detector elements I are produced in a honeycomb pattern from octagonal surfaces, with significantly smaller counting detector elements Z in terms of surface area being inset in the square spaces forming therebetween, thereby not only enabling an energy resolution of the recorded spectrum, but also defining finer measurement beams.

All in all, therefore, at least one embodiment of the present invention proposes a method and/or a computed tomography system for generating tomographic image datasets of a measurement object, the CT system having a plurality of simultaneously operable sets of detector elements which jointly scan a measurement object from a multiplicity of projection angles in an integrating manner on the one hand and an energy-resolving manner on the other, wherein essentially a first projection dataset is determined from measurement data recorded in an integrating manner and at least one second projection dataset is determined from energy-resolved measurement data, and in addition a weighted tomographic result image dataset is calculated based on weighted use of the first and second projection dataset, the weighting being applied to the projection data or the tomographic image data reconstructed therefrom.

Although the invention has been illustrated and described in detail by means of the preferred exemplary embodiment, it is not limited by the disclosed examples, and other variations can be derived herefrom by the person skilled in the art without departing from the scope of protection of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for generating a tomographic result image dataset of a measurement object with the aid of a computed tomography system including at least two simultaneously operable sets of detector elements to jointly scan a measurement object from a multiplicity of projection angles, the method comprising:
    measuring incident radiation over an entire energy spectrum of the incident radiation in an integrating manner via at least one first set of integrating detector elements and defining the measured incident radiation as a first projection dataset;
    measuring incident radiation in at least two energy ranges in a resolving manner via at least one second set of counting detector elements and defining the measured incident radiation in at least two energy ranges as a second projection dataset; and
    calculating the tomographic result image dataset from the first and second projection dataset, wherein a weighting is applied to data originating from the first and second projection dataset.

2. The method of claim 1, wherein, prior to the weighting, a first CT image dataset is reconstructed using the first projection dataset and a second CT image dataset is reconstructed using the second projection dataset.

3. The method of claim 2, wherein the first CT image dataset is overlaid with the second CT image dataset in a weighted manner, each using a respective inter-dataset weighting factor, to produce the CT result image dataset.

4. The method as claimed of claim 2, wherein the first CT image dataset is overlaid with the second CT image dataset in a weighted manner using locally different weighting factors to produce the CT result image dataset.

5. The method of claim 4, wherein at least one of the first and second CT image datasets is subdivided into a multiplicity of subregions in which object-specific characteristics are measured which are systematically mapped with different degrees of quality in the first or second CT image dataset, and the local weighting factor is chosen as a function of the object-specific characteristic.

6. The method of claim 5, wherein a relatively maximum contrast in the subregions is used as the object-specific characteristic.

7. The method of claim 5, wherein fineness of the structures in the subregions is used as the object-specific characteristic.

8. The method of claim 2, wherein a weighting function including at least one coefficient is used for the weighting, and wherein the at least one coefficient is manually variable while studying each respective CT image being newly generated.

9. The method of claim 1, further comprising:
forming a first and a second projection dataset according to a type of the detector elements;
overlaying the first and second projection dataset in a weighted manner to produce a new projection dataset; and
reconstructing a CT result image dataset is from the new projection dataset.

10. The method of claim 5, wherein a respective individual weight extending across the projection dataset is respectively chosen for the first and for the second projection dataset.

11. The method of claim 9, wherein a locally individual weighting of the projection datasets is carried out.

12. The method of claim 11, wherein the locally individual weighting of the projection datasets is carried out at least also as a function of the locally measured photon flux, wherein the measurement data of the integrating detector elements at least tends to be rated relatively more strongly at sites of relatively higher photon flux than the measurement data of the counting detector elements, and wherein the measurement data of the counting detector elements at least tends to be rated more strongly at sites of lower photon flux than the measurement data of the integrating detector elements.

13. The method of claim 11, wherein the locally individual weighting of the projection datasets is carried out at least also as a function of a locally determined spatial frequency, wherein the measurement data of the integrating detector elements at least tends to be rated relatively more strongly at sites of relatively lower values than the measurement data of the counting detector elements, and vice versa.

14. The method of claim 1, wherein, in addition to a CT result image dataset a material separation is carried out at least in relation to subregions of the measurement object at least with the aid of the energy-resolved measurement values of the counting detector elements and the result thereof is overlaid on the CT result image dataset.

15. A computed tomography system, comprising:
at least two simultaneously operable sets of detector elements for simultaneously scanning an examination object from a multiplicity of projection angles, wherein at least one first set of integrating detector elements is configured for integrating radiation measurement and at least one second set of counting detector elements is configured for resolving an incident radiation spectrum into at least two energy bins; and
a computer system for analyzing measurement results of the detector elements, the computer system including a memory and computer programs resident therein, the memory of the computer system including at least one computer program which, during operation, performs measuring incident radiation over an entire energy spectrum of the incident radiation in an integrating manner via at least one first set of integrating detector elements and defining the measured incident radiation as a first projection dataset;
measuring incident radiation in at least two energy ranges in a resolving manner via at least one second set of counting detector elements and defining the measured incident radiation in at least two energy ranges as a second projection dataset; and
calculating the tomographic result image dataset from the first and second projection dataset, wherein a weighting is applied to data originating from the first and second projection dataset.

16. The computed tomography system of claim 15, wherein the at least one first set of integrating detector elements and the at least one second set of counting detector elements are each respectfully arranged on physically different detectors.

17. A computed tomography system of claim 15, wherein the at least one first set of integrating detector elements and the at least one second set of counting detector elements are arranged in one detector.

18. The computed tomography system of claim 17, the integrating detector elements of the at least one first set and the counting detector elements of the at least one second set are arranged grouped in lines in said one detector.

19. The computed tomography system of claim 17, wherein the integrating detector elements of the at least one first set and the counting detector elements of the at least one second set are arranged grouped in rows in said one detector.

20. The computed tomography system of claim 17, wherein the integrating detector elements of the at least one first set and the counting detector elements of the at least one second set are arranged grouped in a checkerboard pattern in said one detector.

21. The computed tomography system of claim 17, wherein the integrating detector elements of the at least one first set are arranged in a plurality of directly adjacent lines and the counting detector elements of the at least one second set are arranged in a plurality of lines adjoining same on at least one detector.

22. The computed tomography system of claim 15, wherein the populated surface of each of the counting detector elements is relatively smaller in area than the surface of each of the integrating detector elements.

23. The method of claim 12, wherein the locally individual weighting of the projection datasets is carried out at least also as a function of a locally determined spatial frequency, wherein the measurement data of the integrating detector elements at least tends to be rated relatively more strongly at sites of relatively lower values than the measurement data of the counting detector elements, and vice versa.

24. The computed tomography system of claim 16, wherein the populated surface of each of the counting detector elements is relatively smaller in area than the surface of each of the integrating detector elements.

25. The computed tomography system of claim 17, wherein the populated surface of each of the counting detector elements is relatively smaller in area than the surface of each of the integrating detector elements.

26. A non-transitory computer readable medium including program segments for, when executed on a computer device, causing the computer device to implement the method of claim 1.

* * * * *